(12) United States Patent
Keady

(10) Patent No.: US 9,123,323 B2
(45) Date of Patent: Sep. 1, 2015

(54) METHOD AND STRUCTURE FOR INDUCING ACOUSTIC SIGNALS AND ATTENUATING ACOUSTIC SIGNALS

(76) Inventor: John P. Keady, Fairfax Station, VA (US)

( * ) Notice: Subject to any disclaimer, the term of this patent is extended or adjusted under 35 U.S.C. 154(b) by 264 days.

(21) Appl. No.: 13/154,429

(22) Filed: Jun. 6, 2011

(65) Prior Publication Data

US 2011/0311079 A1  Dec. 22, 2011

Related U.S. Application Data

(60) Provisional application No. 61/351,290, filed on Jun. 4, 2010.

(51) Int. Cl.
*H04R 25/00* (2006.01)
*G10K 11/162* (2006.01)
*A61F 11/08* (2006.01)
*H04R 1/10* (2006.01)

(52) U.S. Cl.
CPC ............... *G10K 11/162* (2013.01); *A61F 11/08* (2013.01); *H04R 1/1083* (2013.01)

(58) Field of Classification Search
CPC .......... H04R 9/027; H04R 11/02; H04R 1/42; H04R 2225/021; H04R 2225/025; H04R 2400/00; H04R 25/00; H04R 25/43; H04R 25/554; H04R 19/005; H04R 19/04; H04R 1/02; H04R 1/1083; H04R 1/2834; H04R 1/2896; H04R 9/04; G10H 2220/401; G10K 11/162
USPC ......... 381/386, 322, 324, 415, 419, 421, 412; 84/723, 725, 730
See application file for complete search history.

(56) References Cited

U.S. PATENT DOCUMENTS

| | | | | |
|---|---|---|---|---|
| 4,361,879 A | * | 11/1982 | Dubbelday et al. | 367/141 |
| 5,452,268 A | * | 9/1995 | Bernstein | 367/181 |
| 7,132,597 B2 | * | 11/2006 | Hosler | 84/723 |
| 2003/0147538 A1 | * | 8/2003 | Elko | 381/92 |
| 2004/0228494 A1 | * | 11/2004 | Smith | 381/67 |
| 2005/0185813 A1 | * | 8/2005 | Sinclair et al. | 381/380 |
| 2005/0222487 A1 | * | 10/2005 | Miller et al. | 600/25 |
| 2006/0050916 A1 | * | 3/2006 | Wehner | 381/355 |
| 2007/0003087 A1 | * | 1/2007 | Ram et al. | 381/328 |
| 2007/0104344 A1 | * | 5/2007 | Goldberg | 381/324 |

* cited by examiner

*Primary Examiner* — Davetta W Goins
*Assistant Examiner* — Phylesha Dabney

(57) ABSTRACT

At least embodiment is directed to an earpiece comprising a housing; and a field responsive fluid, where the field responsive fluid is in the housing, where the housing is part of the earpiece, and where the earpiece is configured to vary a field to vary an acoustical property of the field responsive fluid.

12 Claims, 5 Drawing Sheets

METHOD AND STRUCTURE FOR INDUCING ACOUSTIC SIGNALS AND ATTENUATING ACOUSTIC SIGNALS

CROSS-REFERENCE TO RELATED APPLICATIONS

This application claims the benefit of U.S. provisional patent application No. 61/351,290 filed 4 Jun. 2010. The disclosure of which is incorporated herein by reference in its entirety.

FIELD OF THE INVENTION

The present invention relates to devices that can be used to control acoustical energy transmitted and more particularly, though not exclusively, a device that can control attenuation or generate acoustical signals.

BACKGROUND OF THE INVENTION

Sudden acoustical shocks, such as a gun blast, explosion, or other high decibel sounds can cause hearing damage and disorientation. Accordingly, a system that can monitor the environment and electrically vary the level of attenuation of the sound heard by a user prior to the shock arriving would be useful.

BRIEF DESCRIPTION OF THE DRAWINGS

Exemplary embodiments of present invention will become more fully understood from the detailed description and the accompanying drawings, wherein.

DETAILED DESCRIPTION OF EMBODIMENTS

Figure 1:
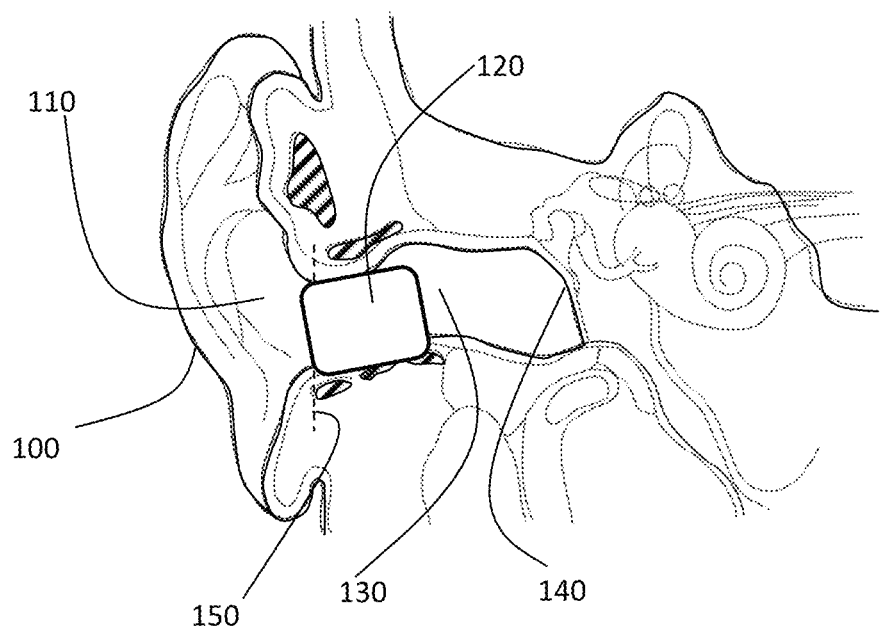
FIG. 1 illustrates general physiology of an ear.

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents). For example, the earpieces can be without transducers (for a noise attenuation application) or one or more transducers (e.g. ambient sound microphone (ASM), ear canal microphone (ECM), ear canal receiver (ECR)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

FerroFluids (FF) and Magnetorheological Fluids (MRF): Ferrofluids can be composed of nanoscale particles (diameter usually 10 nanometers or less) of magnetite, hematite or some other compound containing iron. This is small enough for thermal agitation to disperse them evenly within a carrier fluid, and for them to contribute to the overall magnetic response of the fluid. Ferrofluids are tiny iron particles covered with a liquid coating, also surfactant that are then added to water or oil, which gives them their liquid properties. Ferrofluids are colloidal suspensions—materials with properties of more than one state of matter. In this case, the two states of matter are the solid metal and liquid it is in this ability to change phases with the application of a magnetic field allows them to be used as seals, lubricants, and may open up further applications in future nanoelectromechanical systems. In at least one embodiment a sample of ferrofluid can be mixed with various other fluids (e.g., water, mineral oil, alcohol) to acquire various desired properties. For example when mixed with water and a magnetic field is applied the ferrofluid will separate from the water pushing the water in the opposite direction from the ferrofluid. Such a system can be used as a pump to move fluid from one side of a bladder to another, or even into a separate region, for example where the water can react to an agent when the ferrofluid would not. Another example of a benefit to mixing is to vary the viscosity of the fluid. If the ferrofluid is mixed with mineral oil, the net fluid is less viscous and more easily moved, while remaining mixed when a magnetic field is applied. If the net fluid is in a reservoir chamber one can move the fluid into a different chamber by application of a magnetic field. Note that the discussion above applies equally well for an ER fluid where electric fields are applied instead of magnetic fields.

True ferrofluids are stable. This means that the solid particles do not agglomerate or phase separate even in extremely strong magnetic fields. However, the surfactant tends to break down over time (a few years), and eventually the nano-particles will agglomerate, and they will separate out and no longer contribute to the fluid's magnetic response. The term magnetorheological fluid (MRF) refers to liquids similar to ferrofluids (FF) that solidify in the presence of a magnetic field. Magnetorheological fluids have micrometer scale magnetic particles that are one to three orders of magnitude larger than those of ferrofluids. However, ferrofluids lose their magnetic properties at sufficiently high temperatures, known as the Curie temperature. The specific temperature required varies depending on the specific compounds used for the nanoparticles.

The surfactants used to coat the nanoparticles include, but are not limited to: oleic acid; tetramethylammonium hydroxide; citric acid; soy lecithin These surfactants prevent the nanoparticles from clumping together, ensuring that the particles do not form aggregates that become too heavy to be held in suspension by Brownian motion. The magnetic particles in an ideal ferrofluid do not settle out, even when exposed to a strong magnetic, or gravitational field. A surfactant has a polar head and non-polar tail (or vice versa), one of which adsorbs to a nanoparticle, while the non-polar tail (or polar head) sticks out into the carrier medium, forming an inverse or regular micelle, respectively, around the particle. Steric repulsion then prevents agglomeration of the particles. While surfactants are useful in prolonging the settling rate in ferrofluids, they also prove detrimental to the fluid's magnetic properties (specifically, the fluid's magnetic saturation). The addition of surfactants (or any other foreign particles) decreases the packing density of the ferroparticles while in its activated state, thus decreasing the fluids on-state viscosity, resulting in a "softer" activated fluid. While the on-state viscosity (the "hardness" of the activated fluid) is less of a concern for some ferrofluid applications, it is a primary fluid property for the majority of their commercial and industrial applications and therefore a compromise must be met when considering on-state viscosity versus the settling rate of a ferrofluid.

Ferrofluids in general comprise a colloidal suspension of very finely-divided magnetic particles dispersed in a liquid carrier, such as water or other organic liquids to include, but not limited to: liquid hydrocarbons, fluorocarbons, silicones, organic esters and diesters, and other stable inert liquids of the desired properties and viscosities. Ferrofluids of the type prepared and described in U.S. Pat. No. 3,917,538, issued Nov. 4, 1975, hereby incorporated by reference, may be employed. The ferrofluid is selected to have a desired viscous-dampening viscosity in the field; for example, viscosities at 25.degree. C. of 100 to 5000 cps at 50 to 1000 gauss saturation magnetization of the ferrofluid such as a liquid ferrofluid having a viscosity of about 500 to 1500 cps and a magnetic saturation of 200 to 600 gauss. The magnetic material employed may be magnetic material made from materials of the Alnico group, rare earth cobalt, or other materials providing a magnetic field, but typically comprises permanent magnetic material. Where the permanent magnetic material is used as the seismic mass, it is axially polarized in the housing made of nonferromagnetic material, such as aluminum, zinc, plastic, etc., and the magnet creates a magnetic-force field which equally distributes the enclosed ferrofluid in the annular volume of the housing and on the planar faces of the housing walls.

FIG. 1 illustrates general physiology of an ear. The ear comprises a pinna 100, concha 110, ear canal wall 120, and tympanic membrane 140. Pinna 100 is an external portion of the ear. Pinna 100 is a cartilaginous region of the ear that focuses acoustic information from an ambient environment to an ear canal 130. Concha 110 is also an external portion of the ear. Concha 110 is a bowl shaped region in proximity to the ear canal opening.

A dashed line 150 indicates an opening to the ear (aperture) where sound enters to be received by tympanic membrane 140. The ear canal wall 120 forms an acoustic chamber known as ear canal 130. Ear canal shapes and sizes vary substantially over the human population. Ear canal 130 terminates in tympanic membrane 140. Tympanic membrane 140 is a flexible membrane in the middle ear that couples to components of the inner ear. In general, the acoustic information resident in ear canal 130 vibrates tympanic membrane 120 that is converted to a signal (corresponding to the sound) that is provided to the auditory nerve.

Figure 2:
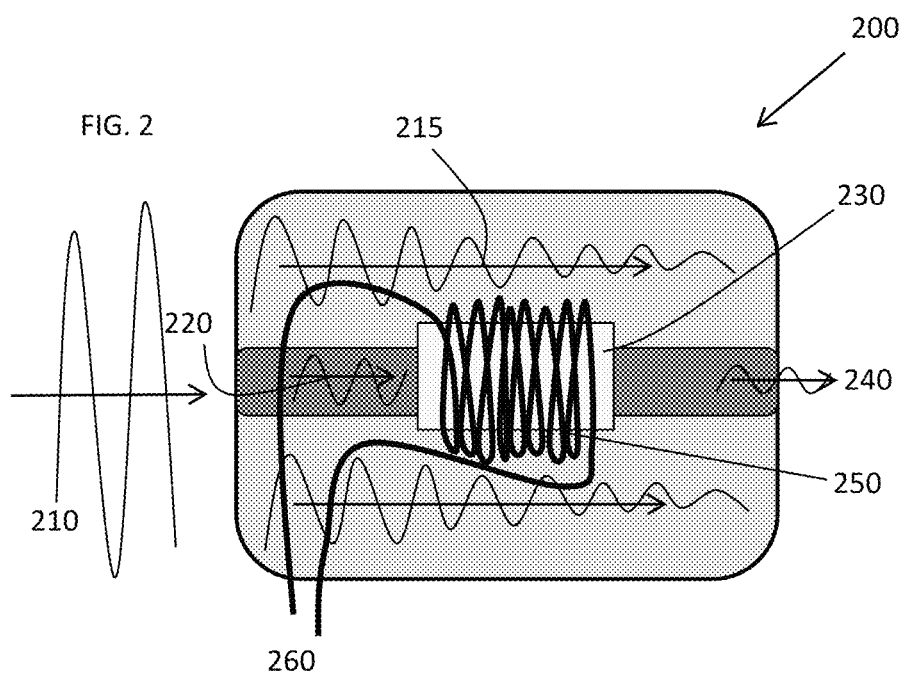
FIG. 2 illustrates an attenuation varying device in accordance with an embodiment.

FIG. 2 illustrates at least one non-limiting example of an electrically controlled acoustic control system that controls the amount of acoustic intensity (which can be frequency dependent) passing through the device 200. In this example acoustical energy is used although such a system can also be used for other various energy inputs (e.g., light, heat, conductivity). An acoustic wave 210 impinges upon the device 200, whereupon a portion 215 travels adjacent to the control tube and is attenuated by the material of device 200 (e.g., foam material for earplugs or polymers for flanges). The portion of the acoustic wave 220 traveling through the control tube passes through Fluid reservoir 230 (e.g., containing FF, MRF, electro fluid (EF and ERF)) and is attenuated an amount dependent upon the applied magnetic or electric field (in the case of an electrofluid) field imposed upon the fluid 230. In the non-limiting example illustrated a magnetic coil 250 provides the method to vary the magnetic field which varies the material properties of MRF and/or FF in eth reservoir 230, thus altering the energy transmitted 240.

A non limiting example of the use of such a system would be for combat earplugs. When an ambient microphone detects a gun shot or other acoustic event of a particular SPL a signal can be sent to a processor directing a certain level of current to be sent to the coil to provide a higher level of attenuation or lower level of transmitted energy 240. Such a system has an advantage over conventional systems since the enhanced acoustic SPL can be detected and reacted to faster than arrival time, providing real time protection of a user.

Figure 3A:
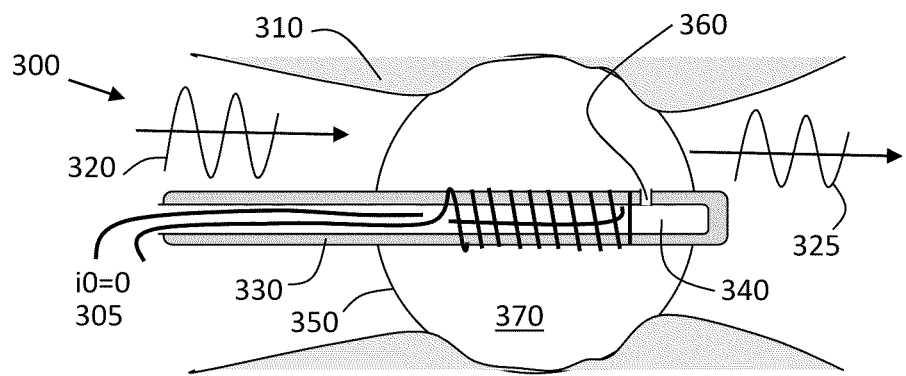
FIGS. 3A-3C illustrates an attenuation varying device in accordance with an embodiment, and acoustic generating devices.
Figure 3B:
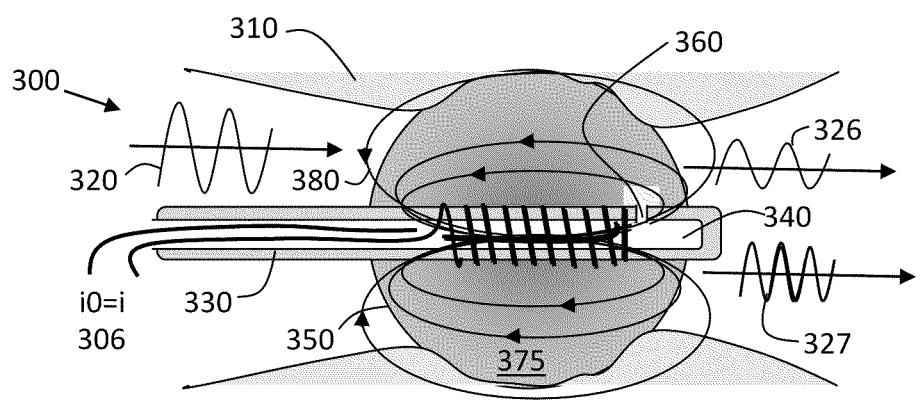
Figure 3C:
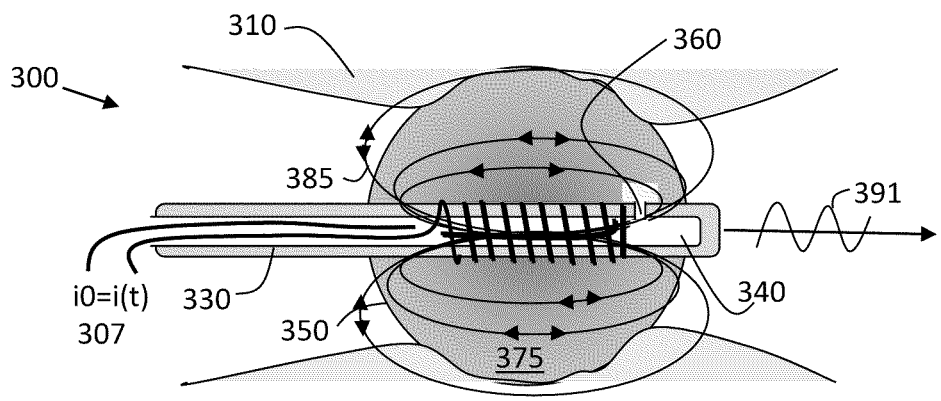
Figure 4A:
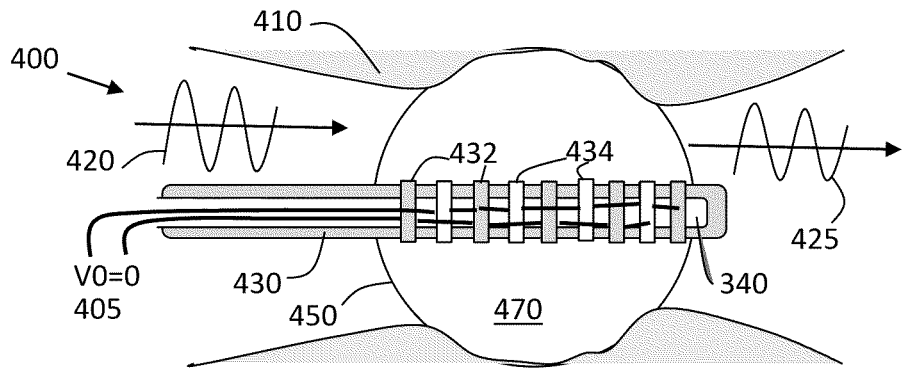
FIGS. 4A-4C illustrates an attenuation varying device in accordance with an embodiment, and acoustic generating devices.
Figure 4B:
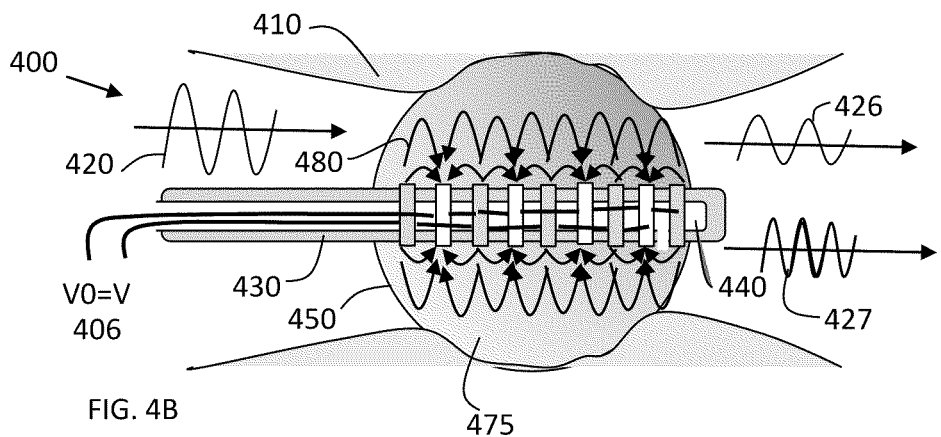
Figure 4C:
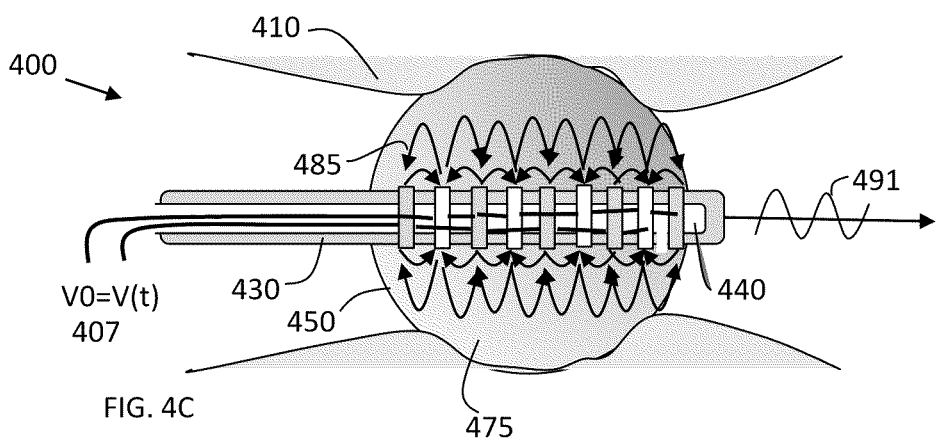

FIGS. 3A-3C illustrates an attenuation varying device in accordance with an embodiment, and acoustic generating devices. In the particular examples described an earpiece such as an earplug is referred to, however the principals discussed are also applicable to stand alone speakers and microphones (e.g., FIG. 5 and FIG. 6). FIGS. 3A-3C illustrate an earpiece 300 inserted into a channel (e.g., pipe, ear canal, vein). An incident energy (e.g. acoustic) 320 is incident upon a housing 350 (e.g., flexible) which includes a field responsive medium (FRM) 370 (e.g., ER, MR). The FRM 370 is delivered through an insertion input 360 to and from the housing 350 via a channel 340 in a tube 330. The non-limiting example illustrated in FIG. 3A illustrates a coil around the tube 330 connected to current source 305. FIG. 3A illustrates no current and thus a passive attenuation is achieved as a function of medium composition of the FRM 370 and the pressure. Thus a portion of the incident energy passes the earpiece in the form of transmitted energy 325. In FIGS. 4A-4C electric fields serve the same function as the magnetic fields in FIGS. 3A-3C. Note that FRM 375 and 475 can have non-homogenous effects. For example acoustical energy can pass along the field lines differently than perpendicular to them, thus one can control the flow of acoustic energy by changing the orientation of magnetic field lines. Likewise one can control the acoustic energy direction by caging electric field lines.

Figure 8:
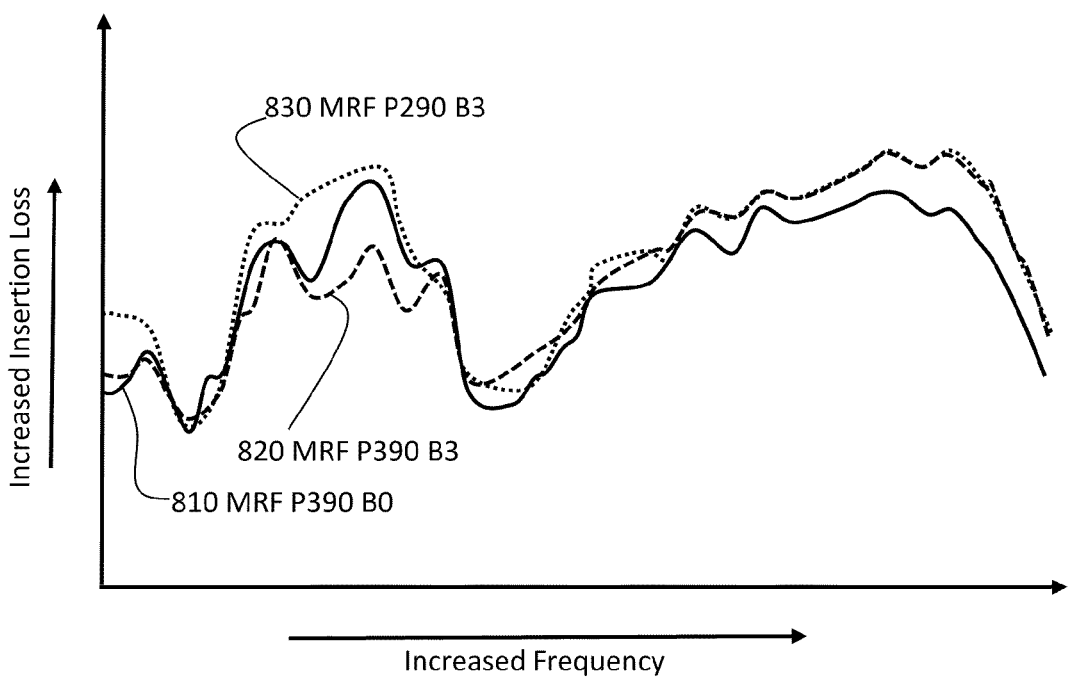
FIG. 8 illustrates insertion loss from a device in accordance with at least one embodiment.

FIG. 3B illustrates the earpiece 300 with a steady current 306 imposed on the coil, creating magnetic field lines 380, which modify the FRM 370 to form FRM 375. FRM 375 reacts to the magnetic field lines 380 and hence its material properties have changed. For example acoustical energy may be reduced while passing through FRM 375, since the fluid is now restricted as to its movement. FIG. 8 illustrates insertion loss values as a function of magnetic field. For example 810 shows the insertion loss (IL) versus frequency for a balloon system filled with an FRM with no imposed magnetic field at a gauge pressure of 390 mbar. 820 shows the same FRM with a strong magnetic field imposed whose field lines are similar as illustrated in FIG. 3B. As is evident the effect of the magnetic field varies as a function of frequency. In comparison 830 illustrates the FRM under the same magnetic field but at a lower pressure of 290 mbar gauge. Note that the pressure also can restrict movement of the fluid. Thus changing the fluid pressure can modify the magnetic/electric field's effect as a function of frequency.

Figure 7:
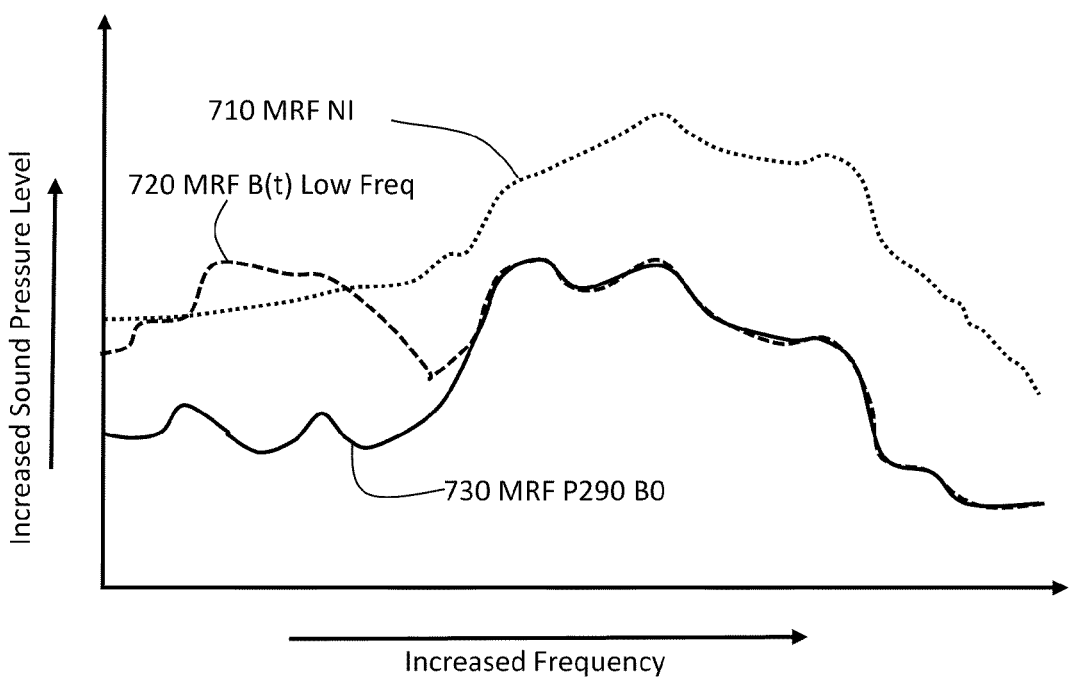
FIG. 7 illustrates sound pressure levels measured from a device in accordance with at least one embodiment.

FIG. 3C illustrates the effect of a temporal variable field generated by varying current 307. The varying magnetic field varies the conditions in the FRM 375, thus oscillating FRM 375. This oscillation can produce energy of its own 391. Thus by varying the current and thus the magnetic field an acoustic signal can be produced by the varying FRM 375. FIG. 7 illustrates sound pressure levels (SPL) as a function of frequency in a channel. 710 illustrates the sound passing through the channel when there is no inflation of the device (e.g., 300). The peak value of 710 is about 114 dB at about 2 kHz. 730 illustrates the SPL when the housing (e.g., 350, 450) is inflated to a pressure of about 290 mbar. Note that for an earpiece pressures can vary from 100 mbar to 3000 mbar depending upon FRM. When a low frequency B(t) (or E(t) is induced FRM (375, 475) varies in response. The variation (e.g., density variation, flows induced) in the FRM move the housing generating energy (e.g., acoustic 391, 491). Such a creation can be seen in FIG. 7 where a low frequency B(t) generated a ow frequency acoustic component of several tens of dBs.

FIGS. 4A-4C illustrates an attenuation varying device in accordance with an embodiment, and acoustic generating devices. FIGS. 4A-4C are similar to FIGS. 3A-3C however FIGS. 4A-4C illustrate embodiments using an FRM that is responsive to electric fields 480, 485. Instead of coils conductive electrodes (e.g. insulted and/or noninsulated) 432, 434 or different voltages causes reaction to FRM 470. Increasing the voltage difference between 432 and 434 creates a larger electric field 480, 485 and the FRM responds by changing (e.g., fluid flow, density changes).

Figure 5:
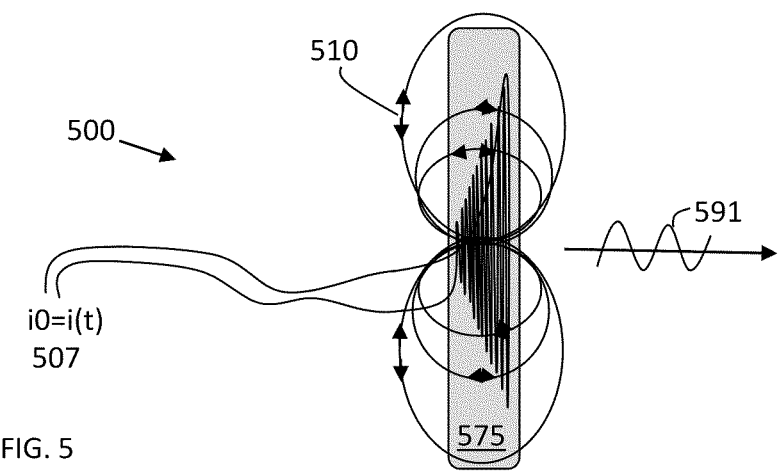
FIG. 5 illustrates a speaker and/or microphone in accordance with at least one embodiment.
Figure 6:
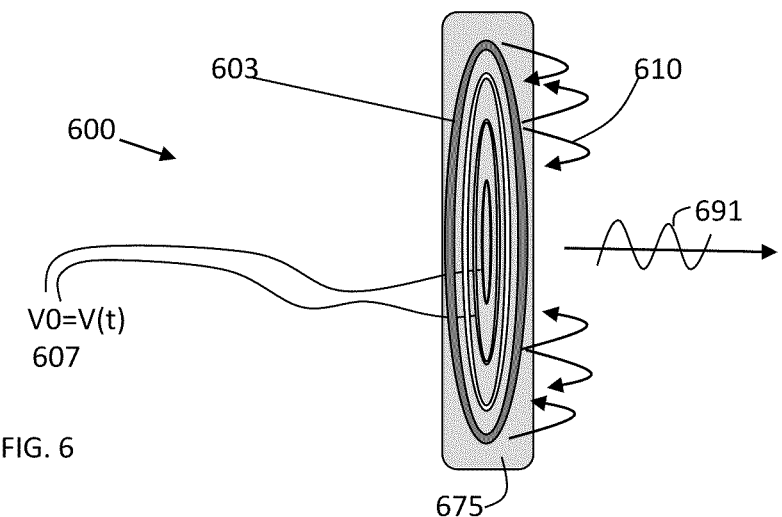
FIG. 6 illustrates a speaker and/or microphone in accordance with at least one embodiment

FIG. 5 illustrates a speaker and/or microphone in accordance with at least one embodiment, and FIG. 6 illustrates a speaker and/or microphone in accordance with at least one embodiment. As discussed with respect to FIGS. 3C and 4C one can vary current and/or voltage to generate acoustical energy 591, and 691. Note also that if a steady field is imposed, for example if 510 and/or 610 were steady, then when sound impinges upon FRM 575 and/or 675 and induced current and/or voltage is generated. The induced current and/or voltage can be converted by known methods to pick up sound making device 500 and 600 microphones. Additionally devices 500 and 600 can have internally induced currents 507 and voltages 607 generating sounds, making the devices speakers.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An earpiece comprising:
   a housing;
   a magnetic field generator coupled to the housing, where the field generator is configured to generate a magnetic field when a non-zero current passes through the field generator, where the field generator is configured to generate a stable magnetic field and a varying magnetic field; and
   a field responsive fluid, where the field responsive fluid is within a portion of the housing, where the field responsive fluid is configured to respond only to the magnetic field from the magnetic field generator and to any ambient magnetic field originating from outside of the portion, where the housing is part of the earpiece, and where the earpiece is configured to use the field generator to generate a field, where the field responsive fluid responds to the field, where the response is at least one of increased sound absorption at a first acoustic frequency and generation of an acoustic wave at a second acoustic frequency.

2. The earpiece according to claim 1, where the earpiece is part of an earplug.

3. The earpiece according to claim 1, where the earpiece is part of a hearing aid.

4. The earpiece according to claim 1, where the field generator is a magnetic field generator which includes a coil.

5. The earpiece according to claim 4, further including an ambient microphone, and a circuit, where the circuit is configured to increase a current in the coil when a threshold sound pressure level is exceeded as measured by the ambient microphone.

6. The earpiece according to claim 4, where the field responsive fluid is magneto responsive fluid.

7. The earpiece according to claim 1, further including an ambient microphone, and a circuit, where the circuit is configured to increase the voltage across the electrodes when a threshold sound pressure level is exceeded as measured by the ambient microphone.

8. An acoustic generator comprising:
   a housing;
   a field varying circuit, where the field varying circuit is a magnetic field generator, where the field generator is configured to generate a magnetic field when a non-zero current passes through the field generator, where the field generator is configured to generate a stable field and a varying field; and
   a field responsive fluid, where the field responsive fluid is in the housing, where the field responsive fluid is configured to respond only to the magnetic field from the magnetic field generator and to any ambient magnetic field originating from outside of the portion, where the field varying circuit is configured to vary a magnetic field so that the field responsive fluid moves in response to the varying magnetic field generating an acoustic signal, where the field has field lines, where the field responsive fluid moves along a first portion of the field lines, where the acoustic signals are generated in a direction along at least a second portion of a field line.

9. The acoustic generator according to claim 8, where the generator is part of a speaker.

10. The acoustic generator to claim 9, where the field generator is an electric field generator which includes electrodes.

11. The earpiece according to claim 9, where the field responsive fluid is magneto responsive fluid.

12. The acoustic generator to claim 9, where the field generator is a magnetic field generator which includes a coil.

* * * * *